United States Patent [19]
Faust et al.

[11] Patent Number: 6,046,281
[45] Date of Patent: Apr. 4, 2000

[54] METHOD FOR COUPLING LIVING CATIONIC POLYMERS

[75] Inventors: Rudolf Faust, Lexington; Savvas E. Hadjikyriacou, Lowell, both of Mass.; Toshio Suzuki, Midland, Mich.

[73] Assignees: University of Massachusetts Lowell, Lowell, Mass.; Dow Corning Corporation, Midland, Mich.

[21] Appl. No.: 08/965,443

[22] Filed: Nov. 6, 1997

[51] Int. Cl.⁷ .......................... C08G 81/02; C08F 299/00
[52] U.S. Cl. .......................... 525/385; 525/383; 525/918; 526/133; 526/346; 526/348.7; 526/348.8
[58] Field of Search .................... 525/385, 918; 526/348.8, 133

[56] References Cited

U.S. PATENT DOCUMENTS

| | | | |
|---|---|---|---|
| 3,994,993 | 11/1976 | Kennedy | 260/877 |
| 4,228,253 | 10/1980 | Marie | 525/247 |
| 4,287,093 | 9/1981 | Gilbert | 252/429 |
| 5,260,378 | 11/1993 | Gandini | 525/156 |
| 5,665,837 | 9/1997 | Faust | 526/237 |

OTHER PUBLICATIONS

Bae et al., Macromolecules (1997), vol. 30, 198–203.
Bae et al., Polymer Preprints (Mar. 1996), vol. 37 (1), 369–370.
Macromolecules 1993, vol. 26, pp. 7315–7321.
Journal of Polymer Science; A Polymer Chemistry, vol. 31, 1531–1542 (1993).
Macromolecules 1997, vol. 30, pp. 198–203.
Macromolecules 1997, vol. 30, pp. 649–651.
Macromolecules 1994, vol. 27, pp. 4648–4651.
Macromolecules 1994, vol. 27, pp. 3453–3458.
Polymeric Materials Science and Engineering, vol. 72, Spring Meeting 1995, Anaheim, California, pp. 173–174.

*Primary Examiner*—Fred Zitomer
*Attorney, Agent, or Firm*—Alex Weitz

[57] ABSTRACT

A method for coupling a living cationic polymer is disclosed, said method comprising reacting the living cationic polymer with an organic compound having at least 2 furan rings in its molecule, said reaction taking place in the presence of a Lewis acid. Preferably, the living cationic polymer is first prepared by polymerizing at least one monomer selected from isobutylene, isoprene or a styrenic monomer using a specific initiator, this reaction also being carried out in the presence of a Lewis acid.

18 Claims, No Drawings

METHOD FOR COUPLING LIVING CATIONIC POLYMERS

FIELD OF THE INVENTION

The present invention relates to a method for coupling a living cationic polymer. More particularly, the invention relates to a method wherein the living cationic polymer is reacted with an organic compound having at least 2 furan rings in its molecule, the reaction taking place in the presence of a Lewis acid.

BACKGROUND OF THE INVENTION

Living anionic polymers are well known in the art. In these systems, the formation of active polymer chain centers during polymerization is faster than chain propagation and the centers remain active until all of the monomer has been consumed. Coupling of such living anionic polymers has been disclosed wherein stable polymeric carbanions are reacted with certain electrophilic species, such as phosgene or dichlorodimethylsilane. This coupling process has been used, for example, in the preparation of telechelic polymers and ABA triblock copolymers.

By contrast, relatively few truly living cationic systems are known and coupling of the living cationic polymers has not been studied to a great extent. Thus, for example, coupling agents for living cationic poly(vinyl ether) and poly (α-methylstyrene) have been reported, but high coupling efficiency was only obtained when the number average degree of polymerization ($DP_n$) was quite low (i.e., ~10) (see articles by Fukui et al. in *J. Polym. Sci., Part A: Polym.Chem.*, 31, 1531(1993); *Macromolecules*, 26, 7315, (1993); *Macromolecules*, 29, 1862 (1996)). Sodiomalonate anions, which were used as coupling agents for living poly(isobutyl vinyl ether), also had drawbacks due to their limited solubility in typical polymerization solvents and use thereof resulted in a low yield for the coupling reaction (Fukui et al. in *Polym.Chem.*, 31, 1531). Non-ionic coupling agents, such as bifunctional silyl enol ethers were successfully employed in the coupling of short living chains ($DP_n$~10) of poly(isobutyl vinyl ether) and displayed high coupling efficiency (i.e., percent of active centers coupled >95%). However, the silyl enol ether is very expensive and this method is not commercially viable, especially for low molecular weight polymers.

In-situ coupling of living polyisobutylene (PIB) has recently been disclosed using bis-diphenylethylenes (bis-DPEs) such as 2,2-bis{4-(1-phenylethenyl)phenyl}propane and 2,2-bis{4-(1-tolylethenyl)phenyl}propane where the two DPE moieties are separated by a spacer group. While the relative amount of coupling agent is negligible in the coupling reaction of high molecular weight PIB, the above process is impractical for the coupling of oligomeric PIB (e.g., number average molecular weight, $M_n$, of about 1000 to 5000) since the relative amount of the expensive coupling agent would be too high (e.g., in the range of about 5 to 15% based on the weight of the coupled product) (see Bae et al. in *Macromolecules*, 30, 198, (1997)).

A facile route has also been developed for the quantitative coupling of oligomeric polyisobutylene (PIB) through c)isopropenyl functionality (—$CH_2C(CH_3)$=$CH_2$) with catalytic amounts of triflic acid ($CF_3SO_3H$) in hexanes at −80° C. (see Coca et al. in *Macromolecules*, 30, 649 (1997)). However this process requires an additional step, namely dehydrohalogenation, to obtain the (ω-isopropenyl functional PIB.

Additionally, U.S. Pat. No. 5,260,378 to Gandini et al. teaches the use of furan derivatives as a binding group (b) in the formation of A-b-B block copolymers. In a typical procedure, a solution of monomer A and the furan derivative is reacted in the presence of a Lewis acid to polymerize the monomer. Excess monomer A is then stripped out and monomer B is added. After polymerization of B, the system is quenched with an alcohol to produce the A-b-B structure. Thus, although the Gandini et al. patent teaches the use of certain furan derivatives as a binding group in a complex polymerization scheme to prepare copolymers having two different polymer blocks, there is no suggestion in this reference to couple an essentially identical living cationic polymer. Moreover, Gandini et al. contemplate the use of furan derivatives having only one furan ring (e.g., their formula (I) wherein x=p=m=n=0). When such a compound was used in an attempt to couple a cationic living polyisobutylene no coupling was observed (i.e., the molecular weight remained essentially the same as that of the uncoupled living polymer).

Thus, there is a need for an efficient and inexpensive agent which allows in-situ coupling of essentially identical living cationic polymers.

SUMMARY OF THE INVENTION

The present invention provides a novel synthetic method for the preparation of homopolymers of the type A-A as well as block copolymers of the type AB-BA, inter alia, wherein A and B represent different polymer blocks. Moreover, telechelic (i.e., functional group containing) versions of such structures can be prepared by the instant method. These structures are obtained by coupling two essentially identical cationic living polymers of the type $A^+$or copolymer of the type $AB^+$, respectively. Thus, we have discovered that furan derivatives which contain at least 2 furan rings are efficient as well as inexpensive coupling agents for the above mentioned living cationic systems. Furthermore, these coupling agents do not have the aforesaid limitations of the prior art and can be used to couple living cationic polymers having low as well as high molecular weight.

The present invention, therefore, relates to a method for coupling a living cationic polymer, said method comprising reacting the living cationic polymer with an organic compound having at least 2 furan rings in its molecule, said reaction taking place in the presence of a Lewis acid.

In a preferred embodiment, the invention further relates to the above method wherein the living cationic polymer is first prepared by polymerizing at least one monomer selected from the group consisting of isobutylene, isoprene and a styrenic monomer, in the presence of a Lewis acid, using an initiator of the formula

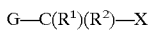

wherein $R^1$ and $R^2$ are selected from hydrogen, alkyl groups having 1 to 20 carbon atoms or aryl groups having 6 to 20 carbon atoms, G is selected from the group consisting of an alkyl group having 1 to 20 carbon atoms, an aryl group having 6 to 10 carbon atoms, a monovalent group containing at least one aliphatic unsaturated group having 2 to 20 carbon atoms, and a group of the formula $X'_2B$—$CH_2$—in which X' is halogen and X is selected from the group consisting of halogen, alkoxy group having 1 to 4 carbon atoms and acyloxy having 2 to 6 carbon atoms. Thus, this embodiment of the invention provides a one-pot procedure for the polymerization and coupling reactions.

The invention further relates to a functional polyisobutylene (PIB) which is prepared by coupling a functional living PIB according to the above method.

DETAILED DESCRIPTION OF THE INVENTION

According to the method of the present invention, a living cationic polymer is reacted with an organic compound having at least 2 furan rings, preferably separated by a spacer organic group, in its molecule in the presence of a Lewis acid, thereby coupling the living polymer to produce a polymer having an increased molecular weight. When preferred combinations of polymer, coupling agent and Lewis acid are employed, an essentially quantitative coupling can be obtained (i.e., the molecular weight of the living polymer is essentially doubled). For the purposes of the invention, the type of cationic polymer is not critical provided it meets the requirements of a living system wherein termination and chain transfer rates are close to zero such that the concentration of active centers remains approximately constant, as noted above. Non-limiting examples of such living cationic systems are well known in the art and include polymers and block copolymers of vinyl ethers, such as methyl vinyl ether, ethyl vinyl ether and isobutyl vinyl ether; functionalized vinyl ethers which have pendant ester, polyoxyethylene or other groups; propenyl ethers; trialkylsilyl vinyl ethers; N-vinylcarbazole; various styrenics, such as p-methyl styrene, p-methoxystyrene and a-methylstyrene; isoprene; and isobutylene.

Some of the living cationic systems known in the art can be functionalized such that, upon coupling according to the present invention, they result in essentially telechelic polymers (i.e., those having functional groups at each end of a molecular chain). For example, a functionalized initiator can be used to polymerize a vinyl ether which is then coupled, as described infra, to provide a telechelic polymer having functional groups (see, for example, descriptions of protected hydroxyl, amino and carboxylic groups in Sawamoto's article in *Cationic Polymerization Mechanism, Synthesis and Applications*, Matyjaszewski, Ed.; Marcel Dekker, New York (1996)).

In the instant method, a preexisting living cationic polymer is coupled with the aid of the furan compound and in the presence of at least one Lewis acid, the latter being limited herein to those Lewis acids which are known to catalyze at least one cationic living polymerization. The interested reader is referred to the article by Matyjaszewski and Pugh in *Cationic Polymerization Mechanism, Synthesis and Applications*, cited supra, for a review of suitable Lewis acids. Examples of such Lewis acids include $BZ_3$, $TiZ_4$, $AlZ_3$, $SnZ_4$ and $ZnZ_2$, inter alia, wherein Z is independently selected from the group consisting of halogen, alkoxy having 1 to 4 carbon atoms and alkyl having 1 to 4 carbon atoms. Preferably Z is halogen, most preferably chlorine. Of course, those skilled in the art will recognize that a compound such as $TiZ_4$ in which all of the Z groups are alkyl groups is not a useful catalyst for cationic living polymerization and such compounds are also not contemplated as suitable catalysts for the coupling reaction.

As stated above, the coupling agent is an organic compound having at least 2 furan rings in its molecule and can have a structure such as

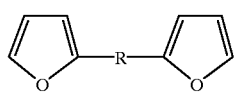

(ii)

wherein R is a straight chain or branched alkylene group having 1 to 10 carbon atoms, preferably at least 2 carbon atoms, which may also contain cyclic structures such as aromatic rings, furan rings, and the like, in either pendant positions or in the alkylene chain. Preferably, the furan coupling agent has the structure

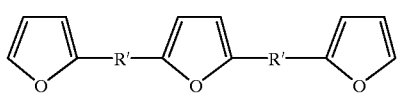

(iii)

wherein R' is independently selected from alkylene groups having 1 to 10 carbon atoms. Specific coupling agents of the invention are exemplified by the following structures:

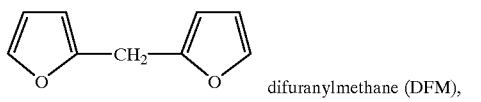

difuranylmethane (DFM),

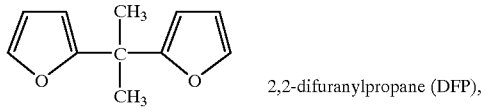

2,2-difuranylpropane (DFP),

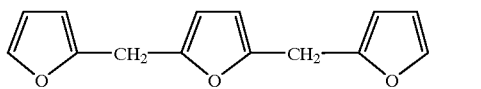

2,5(bis-2-furanylmethylene) furan(bFMF) and

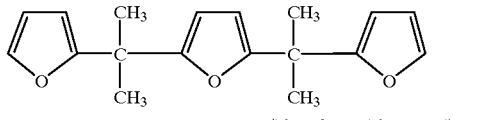

(bis-2-furanyl-isopropyl)-furan (bFPF)

bFMF and bFPF being preferred.

The coupling reaction is typically carried out in an organic solvent solution such as would ordinarily be used to conduct the actual cationic polymerization (e.g., hexane, methylene chloride, methyl chloride, toluene, and combinations thereof). Optimum reaction conditions for a given set of components can be determined by those skilled in the art through routine experimentation, but coupling is typically accomplished at a temperature of about −80° C. to about 40° C. It will be recognized, however, that this temperature will greatly depend upon the particular living polymer under consideration.

For example, in the case of a polyisobutylene living cationic polymer, this temperature is preferably −80° C. to 0C. and ideal conditions for other systems can be arrived at through routine experimentation by one skilled in the art. A stoichiometric amount of the furan coupling agent relative to the concentration of living chain ends is preferred, however, a slight excess of the coupling agent over this stoichiometric equivalent amount of coupling agent for each mole of chain end can be used.

For the case of one preferred embodiment wherein the Lewis acid is $TiCl_4$ and the living polymer is PIB, the Lewis acid is typically added at a level of at least two times the living polymer concentration. In general, optimum Lewis acid levels employed will depend on such factors as Lewis acid type, monomer type and solvent type, inter alia. It has, however, been observed that coupling rate and efficiency is generally improved by using more Lewis acid, preferably 4 to 8 moles for each mole of living polymer. Further addition of Lewis acid is not recommended since this necessitates tedious and expensive purification of the coupled polymer. Furthermore, when the Lewis acid content is already in the above recited typical range (i.e., from the preparation of the preexisting living polymer), further addition may not be necessary.

There is no critical order of addition of the components for the coupling according to the present invention. In a typical procedure, the furan compound and Lewis acid (if a sufficient amount is not provided during the polymerization step) are added to a solution of the living polymer.

When the highly preferred agents bFMF and bFPF are employed to couple nonfunctional polyisobutylene, the coupling efficiency is generally quite high and the number average molecular weight of the preexisting living cationic PIB is essentially doubled, within experimental error (i.e., quantitative coupling). Even when a less preferred furan compound such as DMF or DFP is used, some increase of molecular weight is observed. However, when a compound having only one furan ring such as furan itself is used, the coupling reaction does not proceed and molecular weight remains essentially constant.

In a preferred embodiment of the present method, the living polymer is first prepared by polymerizing at least one monomer selected from the group consisting of isobutylene, isoprene and a styrenic monomer, in the presence of a Lewis acid, using an initiator of the above mentioned formula

G—C($R^1$)($R^2$)—X    (i)

wherein $R^1$ and $R^2$ are selected from the group consisting of hydrogen, alkyl and aryl, preferably each being methyl. In formula (i), X is selected from the group consisting of halogen, alkoxy group having 1 to 4 carbon atoms and acyloxy having 2 to 6 carbon atoms, preferably chlorine. G can be an alkyl group having 1 to 20 carbon atoms, an aryl group having 6 to 10 carbon atoms, such as phenyl, benzyl, tolyl, xylyl, phenethyl, 3-phenylpropyl, ethylphenyl and propyltolyl, or a monovalent group containing at least one aliphatic unsaturated group having 2 to 20 carbon atoms, the latter optionally containing one or more oxygen atoms, such as $H_2C=CH—CO(O)CH_2CH_2—C(CH_3)_2—CH_2—$. Further, G can be a group of the formula

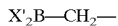

$X'_2B—CH_2—$ in which X' is halogen, preferably chlorine or bromine. A preferred G group is an alkyl group having 1 to 10 carbon atoms, such as methyl, ethyl, isopropyl, butyl, isobutyl, n-hexyl, octyl and decyl. Alternatively, G is preferably a monovalent group having the formula $CH_2=CH—R"—$, in which R" is a divalent hydrocarbyl group having 1 to 10 carbon atoms, such as methylene, ethylene, trimethylene, tetramethylene and hexamethylene.

According to the above preferred embodiment, at least one of the recited monomers is polymerized with the aid of the initiator of formula (i) in the presence of a Lewis acid, the latter being described supra. Preferred Lewis acids for the polymerization include such compounds as TiCl4 and mixtures of $BCl_3$ and $BBr_3$. Additionally, a Lewis base, such as pyridine or its derivatives, such as 2,6-ditert-butylpyridine (DTBP), is preferably included in the polymerization reaction in order to prevent initiation by protic impurities. In a preferred polymerization procedure, the order of addition is solvent, Lewis base, Lewis acid, initiator and monomer.

It will also be apparent to those skilled in the art that the initiator of formula (i) can itself be eliminated and the living cationic polymerization carried out in the presence of only a boron halide catalyst, such as the above mentioned $BCl_3$ and mixtures of the latter with $BBr_3$. This "direct initiation" scheme results in a living cationic polymer having $Cl_2B—$ head groups, as described in U.S. Pat. No. 5,665,837, hereby incorporated by reference. Briefly, such a system is prepared by forming a reaction mixture of an olefin, a Lewis acid, and a base which reacts with essentially all protic impurities in the reaction mixture, thereby preventing protic initiation during polymerization of the olefin. This reaction mixture is reacted to form an initiator in situ which can cause polymerization of additional olefin to form an asymmetric telechelic polymer.

The above described living polymerization reactions are well known in the art, including typical reaction conditions and proportions of the monomer, initiator and Lewis acid, and further description of the preparation of the living cationic polymer is considered unnecessary. Of course, optimization of conditions and proportions needed to obtain a particular living polymer having a desired molecular weight can be achieved through routine experimentation by those skilled in the art (see, for example, above cited article by Sawamoto).

For the purposes of the present invention, the above mentioned styrenic monomer may be selected from such compounds as styrene, p-methylstyrene, α-methylstyrene and indene, inter alia. Preferably, at least 50 mole percent, and more preferably 80 mole percent, of the monomer used in the above cationic polymerization is isobutylene. Most preferably, the entire monomer is isobutylene, this resulting in a living PIB homopolymer.

When the above described polymerization procedure is deemed complete, preferably when monomer conversion is at least 98%, the resulting living polymer is coupled using the furan compound, as described supra. It is contemplated that the coupling reaction can be accomplished in the same vessel used for the polymerization and the solvents, as well as Lewis acid used in the former reaction, can be retained during the coupling reaction (i.e., a one-pot procedure). Of course, additional Lewis acid may be introduced if needed to achieve higher coupling efficiency, as noted supra. After completion of this coupling reaction, as indicated by molecular weight increase or depletion of coupling agent, the resulting polymer may be isolated by conventional techniques, such as precipitation from solution by the addition of a poor solvent for the polymer, as commonly practiced in the art.

In a highly preferred version of the above embodiment, polymerization of isobutylene is initiated with a compound selected from 3,3,5-trimethyl-5-chloro-1-hexene (TMHCl) or 2,4,4-trimethyl-2-chloropentane (TMPCl) using $TiCl_4$ as the Lewis acid. For the case of TMPCl and TMHCl, this reaction is preferably carried out at about −80° C. in a solvent mixture of hexanes/methyl chloride having a volume ratio of about 60/40 to 40/60, and in the presence of a Lewis base (proton trap) such as 2,6-di-tert-butylpyridine (DTBP). The concentration of the initiator, $TiCl_4$ and DTBP are preferably about 0.02 molar (M), 0.02 M and $4 \times 10^{-3}$ M, respectively, based on the total solution. The resulting living PIB polymer according to this embodiment is then coupled using a compound preferably selected from the above mentioned bFMF and bFPF furan derivatives, the latter being particularly preferred in that it typically results in essentially quantitative coupling.

As mentioned above, telechelic polymers may be prepared by the instant method when a functional initiator is used. Thus, when a preferred PIB system which has a functional group Q at one end of its molecule and the living cationic center at the other end is coupled with a preferred furan compound according to formula (ii), the resulting telechelic polymer is represented by the formula

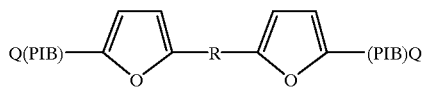

Similarly, when the living PIB is coupled with a preferred furan compound according to formula (iii), the resulting telechelic polymer is represented by the formula

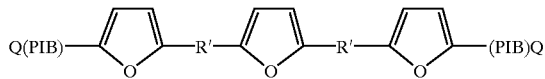

wherein R and R' are defined above, PIB represents the polyisobutylene chain residue and Q is a functional group selected from vinyl, allyl, halogen or —BX"$_2$ where X" is halogen, hydroxy or alkoxy, inter alia. For example, when the initiator is TMHCl, this reaction is preferably carried out at about −80° C. in a solvent mixture of hexanes/methyl chloride having a volume ratio of about 60/40 to 40/60, in the presence of DTBP. The concentration of the initiator, TiCl$_4$ and DTBP are preferably about $2\times10^{-2}$ molar (M), $2\times10^{-2}$ M and $3\times10^{-3}$ M, respectively, based on the total solution. The resulting living telechelic PIB polymer is then reacted with bFPF, as described above, to obtain an essentially quantitative coupling.

Non-functional coupled polymers of the present invention find utility in the preparation of lubricants, thermoplastic elastomers and dispersants. Further, mid-chain functionality can be obtained, or the furan rings can be oxidized to yield −COOH groups.

Telechelic polymers prepared by this method having, e.g., vinyl functionality are particularly suited as base polymers in the formulation of curable sealants, adhesive and coatings when combined with the appropriate catalysts and crosslinkers, inter alia.

EXAMPLES

The following examples are presented to further illustrate the method and compositions of this invention, but are not to be construed as limiting the invention, which is delineated in the appended claims. All parts and percentages in the examples are on a weight basis and all concentrations are moles/liter (M).

Materials

Isobutylene (99%) and methyl chloride (99.5%) were dried by passing them through in-line gas purifier columns packed with BaO/Drierite®. These were condensed in the cold bath of a glove box prior to use.

A hexanes mixture was refluxed for 24 hours with concentrated sulfuric acid, washed with NaOH 10% aqueous solution and then with distilled water until neutral. It was kept over Na$_2$SO$_4$ drying agent for 24 hours, refluxed for 24 hours over CaH2 and distilled under nitrogen.

Methyl 3,3-dimethyl-4-pentenoate (98%), furfuryl alcohol (99%), furan (99+%), %, methyl magnesium bromide 3M (molar) solution in diethyl ether, diethyl ether (99+%), 2,6-di-tert-butylpyridine (97%) and 2,4,4-trimethyl-1-pentene (97%) were obtained from Aldrich Chemical Co. (Milwaukee, Wis.) were used without further purification. Hydrochloric acid was 37% aqueous.

Polymer Purification

All polymers, whether coupled or not, were purified by dissolving them in 20 mL hexanes, filtering to remove inorganics and the PIB was precipitated repeatedly from methanol (20 mL).

Characterization

Molecular weights were measured using a Waters gel permeation chromatography (GPC) system equipped with a Refractometer/Viscometer detector and tunable UV/Viscosity detector. A series of five Ultrastyragel® columns (100, 500, $10^3$, $10^4$ and $10^5$Å) and tetrahydrofuran (THF) solvent at a flow rate of 1 mL/min. were employed using a universal calibration curve based on polystyrene molecular weight standards.

Proton nuclear magnetic resonance ($^1$HNMR) analysis was carried out on Bruker 250 MHz and 500 MHz instruments.

Synthesis of the Initiator 2,4,4 Trimethyl-2-Chloropentane (TMPCl)

Dry gaseous HCl, generated by the reaction of H$_2$SO$_4$ and NaCl, was passed through a 30% solution of 2,4,4-trimethyl-1-pentene in dry and distilled CH$_2$Cl$_2$ at 0° C. for 24 hours. The solvent and excess gaseous HCl were removed and the product was purified by distillation from CaH$_2$ under vacuum to avoid decomposition. TMPCl, when stored in a freezer (−20° C.) under N$_2$, was found to be stable at least for a year. Structure was confirmed by $^1$H NMR.

Synthesis of the Functional Initiator 3,3,5-Trimethyl-5-Chloro-1-Hexene (TMHCl).

A 500 mL three-neck flask equipped with a condenser, a dropping funnel, thermometer, nitrogen inlet and magnetic stirrer was charged with 100 mL of 3M methyl magnesium bromide in diethyl ether. Into the dropping funnel were put 20 mL of methyl-3,3-dimethyl-4-pentenoate dissolved in 70 mL of diethyl ether.

While the flask was being cooled to 0° C. by an ice bath, a dropwise addition of the solution of methyl-3,3-dimethyl-4-pentenoate was started while the temperature was not allowed to rise above 5° C. When the addition was complete, the solution was refluxed for 4 hrs and then cooled to room temperature. The reaction mixture was carefully hydrolyzed by pouring it into a mixture of ice and ammonium chloride (80 g NH$_4$Cl+300 mL of ice). The mixture was stirred very well to effect hydrolysis.

The organic layer was separated from the aqueous layer and the latter was extracted further with two portions of 100 mL diethyl ether. The organic layers were combined and washed twice with 100 mL saturated NaHCO$_3$ aqueous solution and twice with distilled water and then dried overnight over anhydrous sodium sulphate. The next day the drying agent was removed by filtration and evaporation of the diethyl ether on a rotary evaporator provided 17 g of 3,3,5-trimethyl-5-hydroxy-1-hexene (95% yield), ($^1$HNMR 1.07 ppm, s, 6H; 1.20 ppm, s, 6H; 1.65 ppm, s, 2H; 1.83, s, 1H; 4.9–5.1 ppm, q, 2H; 5.9–6.1 ppm, q, 1H.)

Six grams of the 3,3,5-trimethyl-5-hydroxy-1-hexene were dissolved in 120 mL of dry and distilled hexanes. Excess CaCl$_2$ was added and dry HCl gas was bubbled through the solution while it was cooled to 0° C. by means of an ice bath. Bubbling HCl gas was continued overnight. The next day the solution was allowed to warm to room temperature and excess HCl to escape. Filtration to remove CaCl$_2$ and evaporation of the solvent provided 5 g of a material which was then purified by distillation. $^1$HNMR analysis confirmed the target of TMHCl.

Synthesis of Coupling Agents: 2,5-(bis-2-furanylmethylene) furan (bFMF) and difurylmethane (DFM).

A 500 mL flask was charged with 50 mL of furan and 60 mL of furfuryl alcohol. The flask was cooled below 5° C. by means of an ice bath and, while stirring, 20 mL of 37% aq. hydrochloric acid were added dropwise. After the addition of the hydrochloric acid, the ice bath was removed and the reaction mixture allowed to warm to room temperature. Upon stirring for an additional 4 hrs., the system was diluted with hexanes and a viscous, resinous material was separated. The hexanes phase was washed with 10% $Na_2CO_3$ aqueous solution three times and then with distilled water again three times. The organic phase was left over $Na_2SO_4$ overnight and the next day the solvent was removed on a rotary evaporator.

2,5-(bis-2-furanylmethylene)furan and difurylmethane were separated by vacuum distillation and both compounds confirmed by $^1HNMR$ spectroscopy.

Synthesis of the Coupling Agents: 2,2-difuryl-propane (DFP) and 2,5-bis-(2-furyl-propyl)-furan (bFPF).

Furan (50 mL, 46.8 g) and acetone (25 mL, 19.7 g) were placed into a three neck 250 mL flask equipped with a condenser, an addition funnel and a magnetic stirring bar. The mixture was cooled to 0° C. by means of an ice-bath. While stirring, 10 mL of concentrated HCl, (37%) were added dropwise. After the HCl addition, the ice bath was removed allowing the temperature of the reaction mixture to rise to room temperature and the system was stirred for an additional 3 hours. At the end of the three hours the mixture was diluted with an equal volume of hexanes. It was washed until neutral with 10% aqueous sodium carbonate ($Na_2CO_3$) solution and then with distilled water. The mixture was left overnight over drying agent ($Na_2SO_4$).

The next day 24 g of 2,2-difuryl-propane (DFP) and 6 g of 2,5-bis-(2-furyl-propyl)-furane (bFPF) were recovered by distillation under vacuum. The bFPF was further purified by recystallization from methanol to give white needles having a melt point of 47° C.–48° C. $^1HNMR$ analysis confirmed the target compounds.

Example 1

A solvent mixture of hexanes/$CH_3Cl$(60/40 v/v) was charged to a 250 mL reaction flask and cooled to −80° C. $TiCl_4$ was introduced, followed by a solution of 2,6-di-tert-butylpyridine (DTBP) as a proton trap. After mixing for five minutes, 2,4,4-trimethyl-2-chloro-pentane (TMPCl) initiator was introduced, followed by the immediate addition of isobutylene. The concentrations of the reactants were: TMPCl: $2×10^{-2}M$; DTBP; $3×10^{-3}M$; $TiCl_4$: $2×10^{-2}M$; isobutylene: 1M. When conversion reached approximately 100% (total polymerization time=90 minutes), a control sample of the living polymer was removed and quenched with methanol for the determination of initial molecular weight with the following results: $M_n+3000+400$, polydispersity (PD)=$M_w/M_n$=1.2

Portions (20 mL) of the remaining reaction mixture were then distributed into culture tubes and 2,2-difuryl-propane coupling agent at $1×10^{-2}M$ concentration was added to each tube. The concentration of the coupling agent corresponded to 52–54% of the concentration of the initiator, the latter being equivalent to the concentration of the chain ends assuming that the initiation efficiency is about 100% (i.e., each molecule of the initiator has initiated one polymer chain).

After a predetermined reaction time at −80° C., the reaction mixtures were quenched with prechilled methanol. The polymers were purified by repeated precipitation in methanol and, after a reaction time of 3 hours, the $M_n$ increased to 3700±500 (PD=1.19), indicating some coupling.

Example 2

Polymerization of isobutylene was conducted according to the procedure of Example 1. In this experiment, the concentration of $TiCl_4$ was increased to $1.6×10^{-1}M$ during coupling and 2,2-difuryl-propane was used as the coupling agent at a concentration of $1.02×10^{-2}M$. After a coupling time of 3 hours, the $M_n$ increased to 4600±400 (PD=1.15) indicating increased coupling efficiency relative to Example 1.

Example 3

Polymerization of isobutylene was conducted according to the procedure of
Example 1. In this experiment, the concentration of $TiCl_4$ was increased to $4.4×10^{-2}M$ during coupling. The control living polymer had $M_n$=2400 (PD=1.5). In this example, 2,5(bis-2-furanylmethylene) furan was used as the coupling agent at a concentration of $1.04×10^{31}$ $^2M$. After 1 hour, the $M_n$ was 4700±400 (PD=1.4) indicating close to quantitative coupling.

Example 4

Polymerization of isobutylene was conducted according to the procedure of Example 1, including a $TiCl_4$ concentration of $2×10^{-2}M$ to produce a control living polymer having $M_n$=3000 (PD=1.2). In this example 2,5-bis-(2-furyl-propyl)-furan was used as the coupling agent at $1.1×10^{-2}M$ concentration. After 3 hours, the $M_n$ increased to 3900±400 (PD=1.17) indicating some coupling.

Example 5

Polymerization of isobutylene was conducted according to the procedure of Example 1. In this experiment, the concentration of TiCl 14 was increased to $4×10^{-2}M$ during coupling. The control living polymer had $M_n$=3000 (PD=1.2). In this example 2,5-bis-(2-furyl-propyl)-furan was used as the coupling agent at $1.1×10^{-2}M$ concentration. After 3 hours, the $M_n$ increased to 5400±700 (PD=1.14) indicating close to quantitative coupling.

Example 6

Polymerization of isobutylene was conducted according to the procedure of Example 1. In this experiment, the concentration of $TiCl1_4$ was increased to $8×10^{-2}M$ during coupling to produce a control living polymer having $M_n$=3000 (PD=1.2). In this example 2,5-bis-(2-furyl-propyl)-furan was used as coupling agent at $1.02×10^{-2}M$ concentration. After 1 hour, the $M_n$ was 5750±600 (PD=1.15) indicating practically quantitative coupling.

Example 7

The following example illustrates the direct initiation of isobutylene and subsequent coupling using bFPF.

A 500 mL reaction flask equipped with a stirrer was charged with 146 mL of $CH_3Cl$. While stirring, a DTBP solution in methyl chloride was added, followed by the addition of a mixture of $BCl_3$ and $BBr_3$. After 10 minutes, isobutylene was introduced and the latter polymerized for 28 hours at −40° C. Component concentrations calculated on total polymerization volume of 200 mL were:

DTBP: $3×10^{-3}M$; $BCl_3$: 0.5M; $BBr_3$: $6.25×10^3M$; isobutylene: 1M.

After the polymerization, 40 mL of the reaction mixture was withdrawn from the flask and quenched with methanol to determine $M_n$; the remainder of the reaction mix was transferred in amounts of 40 mL to 75 mL culture tubes. The concentration of the chain ends, determined by previous experiments, was found to be $2.66 \times 10^{-2}$M.

Coupling agent (bFPF) was introduced to each culture tube in the form of a solution in methyl chloride, the final concentration of the coupling agent being indicated the second column of Table 1. The coupling reaction was allowed to proceed for 16 hours at $-40°$ C., after which the samples were quenched with methanol. All polymers were purified by reprecipitation 3 times from hexanes/methanol and were characterized by GPC and $^1$H NMR. The $M_n$, as determined by GPC coupled with multi-angle laser light scattering (MALLS), for each polymer is reported in Table 1.

TABLE 1

| Sample | Concentration of bFPF | $M_n$ |
| --- | --- | --- |
| 1 (Control) | 0 | 2600 |
| 2 | $1.45 \times 10^{-2}$M | 4600 |
| 3 | $1.60 \times 10^{-2}$M | 5400 |
| 4 | $1.80 \times 10^{-2}$M | 3700 |
| 5 | $2.00 \times 10^{-2}$M | 3900 |

It is seen that the coupling for samples 2 and 3 was close to quantitative (>95%).

The above samples were confirmed to be telechelic polymers, bearing —B(OCH$_3$)$_2$ or —B(OCH$_3$)OH end groups. Furthermore, oxidation using alkaline H$_2$O$_2$ in THF at room temperature, as described in L. Wang, J. Svirkin and R. Faust; "Direct Initiation In Carbocationic Polymerization" *Polymeric Materials Science and Engineering, Preprint*, 72 173 (1995), resulted in hydroxyl-functional telechelic polymers.

Example 8

The following example illustrates the synthesis of vinyl-functional telechelic isobutylenes by coupling with bFPF.

A 250 mL round bottom reaction flask equipped with a stirrer was charged with 54 mL of hexanes and then cooled to $-80°$ C. Forty six mL of CH$_3$Cl (at $-80°$ C.) were added while stirring, followed by DTBP solution and TiCl$_4$ solution in hexanes/CH$_3$Cl. After 10 minutes the functional initiator TMHCl was introduced followed by the immediate addition of isobutylene. Total reaction volume was 150 mL at $-80°$ C. Concentrations calculated on total polymerization volume were:

DTBP: $3 \times 10^{-3}$M; TiCl$_4$: $2 \times 10^{-2}$M; TMHCl: $2 \times 10^2$M; isobutylene: 1M.

After 30 minutes, the polymerization mixture was transferred to culture tubes, (seven samples at 20 mL/tube). Sample 1 was immediately quenched with methanol and served as the control for $M_n$ determination. Additional TiCl$_4$ solution (in Hexanes/CH$_3$Cl 60/40) was introduced to the other samples and the concentration of this Lewis acid during the subsequent coupling step is indicated in the second column of Table 2. A solution of the coupling agent bFPF in Hexanes/CH$_3$Cl 30/70 was added to each non-control tube to provide the concentration shown in the third column of Table 3 (i.e., concentration during the coupling step). After coupling for 3 hours at $-80°$ C., samples 2–7 were quenched with prechilled methanol. After purification, molecular weights were determined by GPC coupled with viscosity, refractive index and UV detectors, these being reported in the last column of Table 2.

TABLE 2

| Sample | Concentration of TiCl$_4$ | Concentration of bFPF | $M_n$ |
| --- | --- | --- | --- |
| 1 | $2 \times 10^{-2}$M | 0 | 3700 |
| 2 | $4 \times 10^{-2}$M | $7.65 \times 10^{-3}$M | 7000 |
| 3 | $4 \times 10^{-2}$M | $8.67 \times 10^{-3}$M | 6700 |
| 4 | $4 \times 10^{-2}$M | $9.69 \times 10^{-3}$M | 6000 |
| 5 | $8 \times 10^{-2}$M | $7.65 \times 10^{-3}$M | 7200 |
| 6 | $8 \times 10^{-2}$M | $8.67 \times 10^{-3}$M | 6200 |
| 7 | $8 \times 10^{-2}$M | $9.69 \times 10^{-3}$M | 5800 |

It is seen that coupling was essentially quantitative for Examples 2 and 5 (i.e., close to doubling of molecular weight relative to control), these conclusions were also confirmed by $^1$H NMR spectroscopy.

(Comparative) Example 9

The polymerization procedures of Example 7 were repeated at a temperature of $-40°$ C. Component concentrations calculated on total polymerization volume were:

DTBP: $3 \times 10^{-3}$M; BCl$_3$: 0.5M; BBr$_3$: $6.25 \times 10^{-3}$M; isobutylene: 1M.

Coupling of the above prepared living polymer at $-40°$ C. was attempted by introduction of furan at a concentration of $1.33 \times 10^{-2}$M (based on a prior determination of chain end concentration of the living system as $2.66 \times 10^{-2}$M). Analysis of the resulting polymer by $^1$H NMR indicated that the furan ring had not been incorporated into the polymer chain. Further, GPC analysis indicated that $M_n$ of this polymer was 2400 while that of the quenched control (i.e., no furan added) was 2000, this being within experimental error. It was therefore concluded that essentially no coupling was obtained through the use of furan itself.

(Comparative) Example 10

The polymerization procedures of Example 6 were repeated at a temperature of $-80°$ C. Component concentrations calculated on total polymerization volume were:

TMPCl: $2 \times 10^{-2}$M; DTBP; $3 \times 10^{-3}$M; TiCl$_4$: $2 \times 10^{-2}$M; isobutylene: 1M.

Total polymerization time was 70 minutes whereupon the resulting living polymer was separated into three samples. The first of these was quenched without addition of furan and served as a control ($M_n$=2700). The second sample was mixed with additional titanium tetrachloride to bring the level of this Lewis acid to $8 \times 10^{-2}$M, furan ($1.02 \times 10^{-2}$M) was also added and coupling attempted by reacting for 60 minutes at $-80°$ C. ($M_n$=3300). The third sample was treated similarly to the second with the exception that attempted coupling time was extended to 180 minutes ($M_n$=3400).

From $^1$H NMR analysis, it was determined that a significant proportion of the chain ends were chloride and only about 40% of the polyisobutylene chain ends had reacted with the furan. Moreover, strong UV absorbance in the GPC chromatograms and the presence of unidentified peaks between 5.5 ppm and 6.5 ppm in the $^1$H NMR results suggested the presence of more than one furan molecule in some chains and the development of conjugated structures at the chain ends. Thus, the NMR and GPC results indicate that there was essentially no coupling of the living polymer with furan (i.e., the furan ring had, at most, one substitution).

That which is claimed is:

1. A method for coupling a living cationic polymer, said method comprising: reacting the living cationic polymer with an organic compound having at least 2 furan rings in its molecule in the presence of a Lewis acid.

2. The method according to claim 1, wherein said living cationic polymer is polyisobutylene.

3. The method according to claim 2, wherein said organic compound has a formula selected from the group consisting of

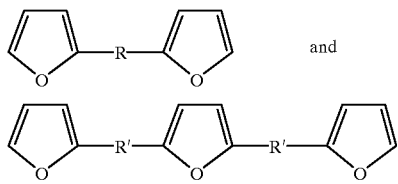

and

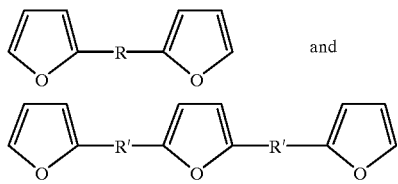

wherein R is an alkylene group having 1 to 10 carbon atoms and R' is independently selected from alkylene groups having 1 to 10 carbon atoms.

4. The method according to claim 3, wherein said organic compound is selected from the group consisting of 2,5(bis-2-furanylmethylene)furan, bis(2-furanyl-isopropyl)-furan and difuranylhexane.

5. The method according to claim 1, wherein said organic compound has a formula selected from the group consisting of

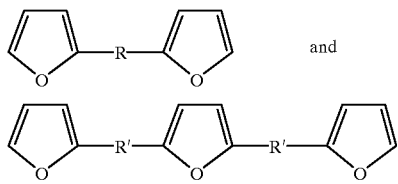

and

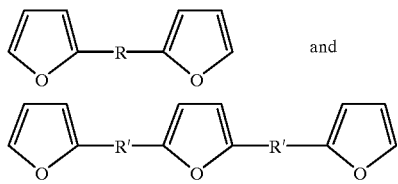

wherein R is an alkylene group having 1 to 10 carbon atoms and R' is independently selected from alkylene groups having 1 to 10 carbon atoms.

6. The method according to claim 5, wherein said organic compound is selected from the group consisting of 2,5(bis-2-furanylmethylene)furan, bis(2-furanyl-isopropyl)-furan and difuranylhexane.

7. The method according to claim 1, wherein said Lewis acid has a formula selected from the group consisting of TiCl$_4$ and BCl$_3$.

8. The method according to claim 1, wherein said living cationic polymer is prepared by polymerizing at least one monomer selected from the group consisting of isobutylene, isoprene and a styrenic monomer using an initiator of the formula

G—C(R$^1$)(R$^2$)—X wherein R$^1$ and R$^2$ are selected from the group consisting of hydrogen, alkyl and aryl, G is selected from the group consisting of an alkyl group having 1 to 20 carbon atoms, an aryl group having 6 to 10 carbon atoms, a monovalent group containing at least one aliphatic unsaturated group having 2 to 20 carbon atoms and a group of the formula X'$_2$B—CH$_2$— in which X' is halogen and X is selected from the group consisting of halogen, alkoxy group having 1 to 4 carbon atoms and acyloxy having 2 to 6 carbon atoms, said polymerizing reaction taking place in the presence of a Lewis acid.

9. The method according to claim 8, wherein said monomer is isobutylene, G is an alkyl group having 1 to 10 carbon atoms, R$^1$ and R$^2$ are methyl and X is halogen.

10. The method according to claim 9, wherein said organic compound has a formula selected from the group consisting of

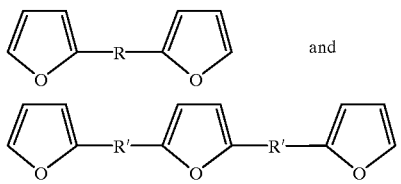

and

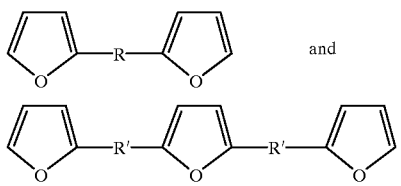

wherein R is an alkylene group having 1 to 10 carbon atoms and R' is independently selected from alkylene groups having 1 to 10 carbon atoms.

11. The method according to claim 10, wherein said organic compound is selected from the group consisting of 2,5(bis-2-furanylmethylene)furan, bis(2-furanyl-isopropyl)-furan and difuranylhexane.

12. The method according to claim 8, wherein said monomer is isobutylene, G is CH$_2$=CH—R"—, in which R" is an alkylene group having 1 to 10 carbon atoms, and X is halogen.

13. The method according to claim 12, wherein said organic compound has a formula selected from the group consisting of

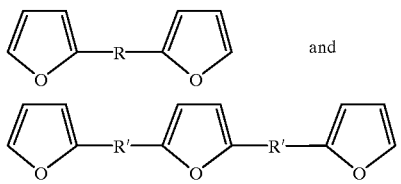

and

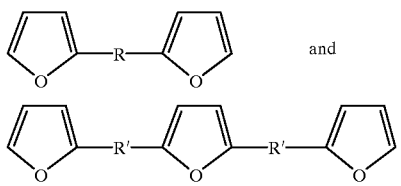

wherein R is an alkylene group having 1 to 10 carbon atoms and R' is independently selected from alkylene groups having 1 to 10 carbon atoms.

14. The method according to claim 13, wherein said organic compound is selected from the group consisting of 2,5(bis-2-furanylmethylene)furan, bis(2-furanyl-isopropyl)-furan and difuranylhexane.

15. The method according to claim 14, wherein said initiator is 3,3,5-trimethyl-5-chloro-1-hexene.

16. The method according to claim 1, wherein said living cationic polymer is prepared by direct polymerization of isobutylene in the presence of a catalyst selected from the group consisting of TiCl$_4$ and mixtures of BCl$_3$ and BBr$_3$.

17. The method according to claim 16, wherein said organic compound has a formula selected from the group consisting of

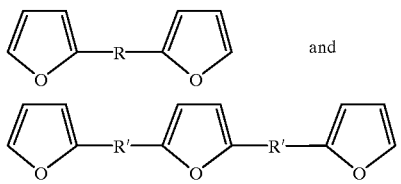

and

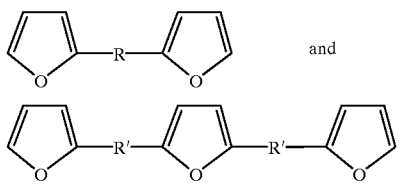

wherein R is an alkylene group having 1 to 10 carbon atoms and R' is independently selected from alkylene groups having 1 to 10 carbon atoms.

18. The method according to claim 17, wherein said organic compound is selected from the group consisting of 2,5(bis-2-furanylmethylene)furan, bis(2-furanyl-isopropyl)-furan and difuranylhexane.

* * * * *